United States Patent [19]

Coppel et al.

[11] Patent Number: 5,891,436
[45] Date of Patent: Apr. 6, 1999

[54] PRIMARY BILIARY CIRRHOSIS AUTOANTIGEN AND METHOD OF USE

[75] Inventors: Ross Leon Coppel, Armadale, Australia; Merrill Eric Gershwin, Davis, Calif.

[73] Assignee: Amrad Corporation Limited, Australia

[21] Appl. No.: 279,818

[22] Filed: Jul. 25, 1994

Related U.S. Application Data

[60] Continuation of Ser. No. 924,812, Aug. 4, 1992, abandoned, which is a division of Ser. No. 259,119, filed as PCT/AU87/00427, Dec. 16, 1987, Pat. No. 5,196,319.

[30] Foreign Application Priority Data

Dec. 16, 1986 [AU] Australia .......................... PH 9523/86

[51] Int. Cl.⁶ .................................................. A61K 39/00
[52] U.S. Cl. .................................... 424/185.1; 424/184.1; 530/300; 530/350
[58] Field of Search .................................. 530/350, 300; 424/88, 184.1, 185.1

[56] References Cited

PUBLICATIONS

Yoon, C.K., "MS Study Yields Mixed Results," *Science* 259:1263, 26 Feb. 1993.
Weiner et al., "Double Blind Pilot Trial of Oral Tolerization With Myelin Antigens in Multiple Sclerosis," *Science* 259:1321–1324, 26 Feb. 1993.
Geysen et al., "Use of peptide synthesis to probe viral antigens for epitodes to a resolution of a single amino acid," Proc. Natl. Acad. Sci., USA 81:3998–4002, Jul. 1984.
Coppel et al. (1988) "Primary Structure of the Human M2 Mitochondrial Auto–antigen of Primary Biliary Cirrhosis: Dihydrolipoamide Acetyltransferase", *Proc. Natl. Acad. Sci. USA 85*, 7317–7321.
Aldesuccio et al J. Immunology vol. 137 pp. 1855–1859 (1986).
Iverson in Handbook of Experience–Immunology Edited by D.M. Wier, Blackwell Scientific Publications 1973 pp. 29.1–29.10.
Frazer et al. (1985) "Reactivity of Anti–Mitochondrial Autoantibodies in Primary Biliary Cirrhosis:Definition of two Novel Mitochondrial Polypeptide Autoantigens", *The Journal of Immunology 135*, 1739–1745.
Kemp et al. (1983) "Expression of *Plasmodium falciparum* Blood–Stage Antigens in *Escherichia coli*:Detection with Antibodies from Immune Humans", *Proc. Natl. Acad. Sci. USA 80*, 3787–3791.
Mendel–Hartvig et al.(1985) "Primary Biliary Cirrhosis:Further Biochemical and Immunological Characterization of Mitochondrial Antigens", *Clin. exp. Immunol. 62*, 371–379.
Stephens et al. (1983) "The Pyruvate Dehydrogenase Complex of *Escherichia coli* K12",*J. Eur. Biochem. 133*, 481–489.
Young et al. (1983) "Efficient Isolation of Genes by using Antibody Probes", *Proc. Natl. Acad. Sci. USA 80*, 1194–1198.

*Primary Examiner*—Robert D. Budens
*Attorney, Agent, or Firm*—Scully, Scott, Murphy & Presser

[57] ABSTRACT

Isolated peptides and polypeptides exhibiting the antigenicity of the 70 kD mitochondrial autoantigen of primary biliary cirrhosis are provided. The peptides, polypeptides and antigenic fragments thereof are useful in the diagnosis and treatment of primary biliary cirrhosis.

9 Claims, 11 Drawing Sheets

```
GlyProGluAlaPheLysAsnTyrThrLeuAspSerAlaThr
GGGCCTGAGGCTTTTAAAAATTATACATTGGATTCAGCAACA
    10        20        30        40

ProAlaAlaProSerAlaSerAlaProGlySerSerTyrPro
CCAGCTGCACCTTCTGCAAGTGCTCCAGGTAGCTCCTATCCC
   100       110       120       130

GlyThrValGlnArgTrpGluLysLysValGlyGluLysLeu
GGCACCGTCCAGAGGTGGGAAAAGAAAGTGGGAGAGAAGCTG
   190       200       210       220

GlyPheGluValGlnGluGluGlyTyrLeuAlaLysIleLeu
GGCTTTGAAGTACAAGAAGAAGGTTATCTGGCAAAAATCCTG
   280       290       300       310

IleValGluLysGlnGluAspIleAlaAlaPheAlaAspTyr
ATAGTAGAAAAACAGGAAGATATAGCAGCATTTGCAGACTAC
   370       380       390       400

ProProProValAlaAlaValProProIleProGlnProLeu
CCACCCCCAGTGGCAGCTGTTCCTCCCATCCCCCAGCCTTTA
   460       470       480       490

ValSerProLeuAlaLysLysLeuAlaAlaGluLysGlyIle
GTTAGCCCTCTTGCAAAGAAATTGGCAGCAGAGAAAGGGATT
   550       560       570       580

LysAspIleAspSerPheValProThrLysAlaAlaProAla
AAGGACATTGACTCTTTTGTGCCTACTAAGGCTGCTCCTGCC
   640       650       660       670
```

FIG. 6a.

```
AlaAlaThrGlnAlaAlaProAlaProAlaAlaAlaProAlaAlaAla
GCTGCCACACAGGCAGCCCCAGCCCCAGCTGCAGCTCCAGCTGCTGCC
    50        60        70        80        90

ValHisMetGlnIleValLeuProAlaLeuSerProThrMetThrMet
GTTCACATGCAGATTGTTCTTCCTGCCCTCTCCCCAACCATGACCATG
    140       150       160       170       180

SerGluGlyAspLeuLeuAlaGluIleGluThrAspLysAlaThrIle
AGTGAAGGAGACTTGCTGGCAGAGATAGAGACCGACAAGGCCACCATA
    230       240       250       260       270

ValProGluGlyThrArgAspValProLeuGlyThrProLeuCysIle
GTCCCTGAAGGCACAAGGGATGTTCCTCTGGGAACCCCGCTATGTATC
    320       330       340       350       360

ArgProThrGluValThrSerLeuLysProGlnAlaProProProVal
AGGCCAACAGAAGTGACCAGCTTAAAGCCACAGGCACCACCACCTGTC
    410       420       430       440       450

AlaProThrProSerAlaAlaProAlaGlyProLysGlyArgValPhe
GCACCTACCCCCTCAGCCGCTCCTGCTGGACCAAAGGGAAGGGTGTTC
    500       510       520       530       540

AspLeuThrGlnValLysGlyThrGlyProGluGlyArgIleIleLys
GACCTCACCCAAGTTAAAGGGACGGGACCAGAAGGCAGAATCATCAAG
    590       600       610       620       630

AlaAlaAlaAlaAlaProProGlyProArgValAlaProThrProAla
GCTGCAGCAGCTGCTCCCCGGGTCCAAGAGTGGCACCAACTCCTGCA
    680       690       700       710       720
```

FIG. 6b.

```
GlyValPheIleAspIleProIleSerAsnIleArgArgVal
GGTGTCTTCATAGACATCCCCATCAGCAACATTCGTCGAGTG
    730         740        750        760

LeuSerValAspValAsnMetGlyGluValLeuLeuValArg
CTTTCTGTTGATGTAAATATGGGAGAGGTGCTGTTGGTGCGG
    820         830        840        850

AspPheIleIleLysAlaSerAlaLeuAlaCysLeuLysVal
GACTTCATCATAAAAGCTTCAGCTTTGGCCTGCCTGAAAGTT
    910         920        930        940

ValValAspValSerValAlaValSerThrProAlaGlyLeu
GTGGTTGATGTCAGCGTTGCTGTCAGTACCCCTGCAGGACTT
   1000        1010       1020       1030

AlaSerAspValValSerLeuAlaSerLysAlaArgGluGly
GCTAGTGATGTTGTTTCTTTAGCCTCCAAAGCAAGAGAGGGT
   1090        1100       1110       1120

LeuGlyMetPheGlyIleLysAsnPheSerAlaIleIleAsn
TTAGGGATGTTCGGAATTAAGAATTTCTCTGCGATTATTAAC
   1180        1190       1200       1210

IleProAlaAspAsnGluLysGlyPheAspValAlaSerVal
ATCCCTGCAGATAATGAGAAAGGCTTTGACGTGGCTAGTGTG
   1270        1280       1290       1300

LeuGluProSerGlyLeuLeu
TTGGAGCCCAGTGGCTTGCT
   1360        1370
```

*FIG. 6c.*

```
IleAlaGlnArgLeuMetGlnSerLysGlnThrIleProHisTyrTyr
ATTGCGCAGAGGCTCATGCAGTCGAAGCAGACTATACCTCATTATTAC
    770       780       790       800       810

LysGluLeuAsnLysMetLeuGluGlyLysGlyLysIleSerValAsn
AAGGAACTTAATAAGATGCTTGAAGGTAAAGGAAAAATCTCCGTCAAT
    860       870       880       890       900

ProGluAlaAsnSerSerTrpMetAspThrValIleArgGlnAsnHis
CCTGAAGCAAACTCATCTTGGATGGACACAGTTATACGACAAAATCAT
    950       960       970       980       990

IleThrProIleValPheAsnAlaHisIleLysGlyLeuGluThrIle
ATCACCCCTATTGTGTTTAATGCACACATAAAAGGACTGGAAACCATT
   1040      1050      1060      1070      1080

LysLeuGlnProHisGluPheGlnGlyGlyThrPheThrIleSerAsn
AAACTTCAGCCTCACGAGTTCCAGGGTGGGACATTTACAATCTCCAAC
   1130      1140      1150      1160      1170

ProProGlnAlaCysIleLeuAlaIleGlyAlaSerGluAspLysLeu
CCACCTCAGGCATGTATTTTGGCAATTGGTGCTTCCGAGGATAAACTG
   1220      1230      1240      1250      1260

MetSerValThrHisSerAlaValIleIleGluLeuTrpMetGluGln
ATGTCTGTCACACACTCAGCTGTGATCATCGAGTTGTGGATGGAGCAG
   1310      1320      1330      1340      1350
```

FIG. 6d.

```
ProGlySerSerTyrProProHisMetGlnValLeuLeuProAla
CCTGGTAGCTCATATCCCCCTCACATGCAGGTACTTCTTCCTGCC
      10        20        30        40

LysValGlyGluLysLeuSerGluGlyAspLeuLeuAlaGluIle
AAAGTGGGTGAGAAGCTAAGTGAAGGAGACTTACTGGCAGAGATA
     100       110       120       130

TyrLeuAlaLysIleLeuValProGluGlyThrArgAspValPro
TATCTGGCAAAAATCCTGGTCCCTGAAGGCACAAGAGATGTCCCT
     190       200       210       220

SerAlaPheAlaAspTyrArgProThrGluValThrAspLeuLys
TCAGCATTTGCTGACTATAGGCCAACCGAAGTAACAGATTTAAAA
     280       290       300       310

ProThrProGlnProLeuAlaProThrProSerAlaProCysPro
CCAACTCCCCAGCCTTTAGCTCCTACACCTTCAGCACCCTGCCCA
     370       380       390       400

AlaLysLysLeuAlaValGluLysGlyIleAspLeuThrGlnVal
GCAAAGAAGTTGGCAGTAGAGAAAGGGATTGATCTTACACAAGTA
     460       470       480       490

SerPheValProSerLysValAlaProAlaProAlaAlaValVal
TCTTTTGTGCCTAGTAAAGTTGCTCCTGCTCCGGCAGCTGTTGTG
     550       560       570       580

ThrAspIleProIleSerAsnIleArgArgValIleAlaGlnArg
ACAGATATCCCAATCAGCAACATTCGTCGGGTTATTGCACAGCGA
     640       650       660       670

AspValAsnMetGlyGluValLeuLeuValArgLysGluLeuAsn
GATGTAAATATGGGAGAAGTTTTGTTGGTACGGAAAGAACTTAAT
     730       740       750       760

IleLysAlaSerAlaLeuAlaCysLeuLysValProGluAlaAsn
ATAAAAGCTTCAGCTTTGGCATGTTTAAAAGTTCCCGAAGCAAAT
     820       830       840       850

ValSerValAlaValSerThrProAlaGlyLeuIleThrProIle
GTCAGTGTTGCGGTCAGTACTCCTGCAGGACTCATCACACCTATT
     910       920       930       940
```

*FIG. 8a.*

```
  LeuSerProThrMetThrMetGlyThrValGlnArgTrpGluLys
  CTCTCTCCCACCATGACCATGGGCACAGTTCAGAGATGGGAAAAA
       50        60        70        80        90

GluThrAspLysAlaThrIleGlyPheGluValGlnGluGluGly
  GAAACTGACAAAGCCACTATAGGTTTTGAAGTACAGGAAGAAGGT
      140       150       160       170       180

LeuGlyThrProLeuCysIleIleValGluLysGluAlaAspIle
  CTAGGAACCCCACTCTGTATCATTGTAGAAAAAGAGGCAGATATA
      230       240       250       260       270

ProGlnValProProProThrProProProValAlaAlaValPro
  CCACAAGTGCCACCACCTACCCCACCCCCGGTGGCCGCTGTTCCT
      320       330       340       350       360

AlaThrProAlaGlyProLysGlyArgValPheValSerProLeu
  GCTACTCCTGCTGGACCAAAGGGAAGGGTGTTTGTTAGCCCTCTT
      410       420       430       440       450

LysGlyThrGlyProAspGlyArgIleThrLysLysAspIleAsp
  AAAGGGACAGGACCAGATGGTAGAATCACCAAGAAGGATATCGAC
      500       510       520       530       540

ProProThrGlyProGlyMetAlaProValProThrGlyValPhe
  CCTCCCACAGGTCCTGGAATGGCACCAGTTCCTACAGGTGTCTTC
      590       600       610       620       630

LeuMetGlnSerLysGlnThrIleProHisTyrTyrLeuSerIle
  TTAATGCAATCAAAGCAAACCATACCTCATTATTACCTTTCTATC
      680       690       700       710       720

LysIleLeuGluGlyArgSerLysIleSerValAsnAspPheIle
  AAGATATTAGAAGGGAGAAGCAAAATTTCTGTCAATGACTTCATC
      770       780       790       800       810

SerSerTrpMetAspThrValIleArgGlnAsnHisValValAsp
  TCTTCTTGGATGGACACAGTTATAAGACAAAATCATGTTGTTGAT
      860       870       880       890       900

ValPheAsnAlaHisIleLys
  GTGTTTAATGCACATATAAAA
      950       960
```

PRIMARY BILIARY CIRRHOSIS AUTOANTIGEN AND METHOD OF USE

This application is a continuation of application Ser. No. 07/924,812, filed Aug. 4, 1992, now abandoned, which is a divisional of application Ser. No. 07/259,119, filed Sep. 22, 1988, now U.S. Pat. No. 5,196,319, which is a 371 national stage of International Application PCT/AU87/00427, filed Dec. 16, 1987, the contents of which are hereby incorporated by reference.

FIELD OF THE INVENTION

This invention relates to the identification, cloning and expression of an auto-antigen which is recognised as a target in the characteristic autoantibody response in primary biliary cirrhosis (PBC), and to the use of this protein, fragments thereof or fused polypeptides containing the protein or fragments thereof in diagnostic tests for PBC, and in treatment of patients suffering from PBC.

BACKGROUND OF THE INVENTION

Primary biliary cirrhosis (PBC) is a chronic disease characterised by progressive inflammatory obliteration of the intrahepatic bile ducts. The disease is marked by an autoantibody response to mitochondria[1-4], originally identified using immunofluorescence[5]. With the recent use of immunoblotting, specific proteins have been recognized as targets of the anti-mitochondrial antibodies (AMA) of PBC[2,6,7]. In particular, serum antibodies to a 70 kilodalton (kd) protein have been found in greater than 95% of patients with PBC but not in patients with other autoimmune liver diseases,[2,8]; two other proteins of 45 and 39 kd are less frequently detected in PBC sera[1,2,9]. The identity of each of these autoantigens has been unknown, as is the relationship of these antigens to the pathogenesis of the disease. However, the 70 kd antigen is highly conserved in evolution, being present in mammals, yeast and bacteria[10] and it is therefore believed to have an important structural or biological function[2].

Despite the paucity of data on mechanisms of antimitochondrial antibody formation, by enzyme-linked immunosorbent assay (ELISA), clinically more than 95% of patients with PBC can be found to have such anti-mitochondrial antibodies[2,6]. When crude mitochondrial antigen preparations are used, subjects with a variety of diseases, including patients with liver diseases other than PBC, certain connective tissue diseases, and drug reactions, and occasionally even healthy individuals, can also be demonstrated to have antibodies to mitochondria. Accordingly, assays using such crude preparations are unable to provide specific diagnosis of PBC. By way of example, German Patent Publication No. 3,237,602 discloses an ELISA for detection and determination of antimitochondrial antibodies in serum using a crude mitochondrial antigen preparation. The lack of specificity of the assay is evident from the suggested use of the assay in the specific diagnosis of disorders such as PBC as well as the cholestatic form of chronic active hepatitis, syphilis (II), drug-induced pseudo lupus erythematodes syndrome, certain primary non-hepatic immunopathies, iproniazid-induced hepatis and side effects of certain medicaments such as beta-receptor blockers. By more vigorous isolation of mitochondrial membranes, the problem of antigenic heterogeneity becomes clearer and has led to definitions of specific mitochondrial antigens based on trypsin sensitivity and location of antigens within inner vs outer mitochondrial membranes. Notwithstanding this, however, the diagnosis of PBC still relies heavily on the demonstration of anti-mitochondrial antibodies by the relatively insensitive procedure of immunofluorescence or by more sensitive, but still relatively nonspecific, methods, including complement fixation, ELISA, and immunoprecipitation[23-28].

SUMMARY OF THE INVENTION

The present invention is based on the identification of a cDNA clone derived from a rat liver gene expression library that expresses the 70 kd mitochondrial autoantigen of PBC, (called M2 by some groups of investigators[1,9]) and on sequence determination thereof. The sequence is encoded by nuclear and not mitochondrial DNA.

The present invention thus provides the basis of an extremely sensitive and specific diagnostic ELISA for anti-70 kd antibodies found in PBC.

According to a first aspect of the present invention, there is provided a DNA molecule comprising a nucleotide sequence substantially corresponding to all or a portion of the base sequence coding for the 70 kd mitochondrial autoantigen of primary biliary cirrhosis (PBC), or an antigenically active fragment thereof.

Preferably, the DNA molecule in accordance with this aspect of the invention is characterised by at least a portion thereof comprising a base sequence substantially as shown in FIG. 6, or a fragment thereof.

In another aspect, this invention provides a recombinant DNA molecule comprising a nucleotide sequence as described above, operatively linked to an expression control sequence. Such a recombinant DNA molecule may for example comprise an expression vector such as a bacteriophage or plasmid, or a host cell such as a bacterium or other microorganism transformed therewith.

In yet another aspect of this invention there is provided a synthetic peptide or polypeptide displaying the antigenicity of all or a portion of the 70 kd mitochondrial autoantigen of primary biliary cirrhosis, or an antigenically active fragment thereof.

Preferably, the synthetic peptide or polypeptide of this aspect of the invention is characterised by at least a portion thereof comprising an amino acid sequence substantially as shown in FIG. 6 or FIG. 8, or an antigenically active fragment thereof.

Such a synthetic peptide or polypeptide may, for example, be prepared by expression of a host cell transformed with a recombinant DNA molecule as broadly described above, either as a fused polypeptide or directly. Alternatively, it may be prepared by chemical synthesis, such as by the well-known Merrifield solid-phase synthesis procedure.

The present invention extends to the synthetic peptide corresponding to the entire 70 kd autoantigen, and to nucleotide sequences coding for the entire autoantigen, as well as to fragments thereof. By way of example, one such fragment is the fragment encoded by nucleotides 76–679 of FIG. 6. This fragment of approximately 200 residues is capable of adsorbing out of a patient serum all antibodies directed against the native autoantigen. Within this fragment is a 20 residue fragment of amino acid sequence:

A E I E T D K A T I G F E V Q E E G Y L which has been demonstrated to have substantial reactivity with autoantibodies. This fragment is common to the sequences of both FIG. 6 and FIG. 8. The present invention therefore extends to the use of antigenically active fragments such as these, as well as to the use of the entire autoantigen, in diagnostic assays.

The present invention also extends to the use of the synthetic peptide or polypeptide, or fragment, of this invention as an antigen in a diagnostic test for PBC by detection or determination of the titre of antimitochondrial antibody in a patient's serum, for example using ELISA or RIA technology or an agglutination assay using antigen-coated beads or the like. The invention also extends to use of the synthetic peptide or polypeptide, or fragment, in the treatment of patients. In this latter aspect, such methods of treatment include the use of the synthetic antigen, as an adsorbent to remove PBC antibodies or reactive cells from a patient, as well as the use of these active components in direct administration to a patient as a desensitizing agent to eliminate or diminish reactivity of the patient to the PBC autoantigen.

In addition to use of the synthetic autoantigen in the detection of anti-mitochondrial antibody in a serum sample, the present invention extends to use of the synthetic peptide or polypeptide, or fragment, in the measurement of class-specific immunoglobulin titres using specific typing reagents. Applications also extend to the measurement of the affinity of either the whole autoantibody, or the affinity of individual classes or subclasses of the autoantibody. Affinity may be measured by a number of procedures, for example, by replicate ELISA assays performed using different washes of guanidine thiocyanate[42]. A further extension of the diagnostic assay is the measurement of the degree of interference of autoantibodies with the enzymic function of the 70 kd autoantigen (now shown to be lipoate acetyl transferase, see later). The source of the enzyme may be derived from expression of full length clones as native polypeptides or fusion polypeptides, or from expression of enzymatically active fragments or purified protein from mitochondria. The enzyme assay is a standard assay well known in the art, but modified to include a step of incubation with sample serum or cells. In yet a further extension of the use of the synthetic peptide or polypeptide, or fragment, there is included the measurement of reactivity of patient cells to the autoantigen. The synthetic peptide or polypeptide, or fragment, may be added, in solution or bound to a solid support, to patient cells derived from peripheral blood or from tissue biopsies either unfractionated, fractionated or as a continuous cell line. Reactivity to the autoantigen may then be measured by standard proliferation assays such as incorporation of tritiated thymidine, standard cytotoxic assays such as release of marker radioactivity from target cells, or other standard assays of cellular reactivity which are well known in the art.

In one particularly important aspect of this invention, there is provided a diagnostic test for detection of antimitochondrial antibody in a serum sample, which comprises the steps of:

(i) contacting said serum sample with a synthetic peptide or polypeptide displaying portion of the 70 kd mitochondrial autoantigen of PBC, or an antigenically active fragment thereof, said synthetic peptide or polypeptide being immobilized on a support, and (ii) detecting the presence of anti-mitochondrial antibody in said serum bound to said synthetic peptide or polypeptide.

In this aspect, the invention also provides a diagnostic test kit for detection of anti-mitochondrial antibody in a serum sample, which comprises:

(i) a support having immobilised thereon a synthetic peptide or polypeptide displaying the antigenicity of all or a portion of the 70 kd mitochondrial autoantigen of PBC, or an antigenically active fragment thereof, and (ii) means for detecting the presence of anti-mitochondrial antibody in said serum bound to said synthetic peptide or polypeptide.

Preferably the detection of the presence of bound AMA is by use of well known RIA or ELISA techniques.

As a result of the production of a recombinant fused polypeptide displaying the antigenicity of the 70 kd mitochondrial autoantigen of PBC, this autoantigen has now been identified as lipoate acyltransferase. In addition, the immunoglobulin isotypes of the anti-mitochondrial antibodies has been determined, and IgG3 has been found to be the predominant isotype in a group of PBC patients, with IgM next most prevalent. Comparison of serum immunoglobulin isotype levels of PBC patients with healthy normal adults has shown that serum IgG3 and IgM were very elevated in PBC; IgG3 at 5.5 fold and IgM at 4.3 fold above normal.

In accordance with the present invention, expression of the cDNA insert encoding the mitochondrial autoantigen, or fragments thereof, may be achieved in a number of different ways. The detailed description herein provides examples of expression as β-galactosidase fusion proteins in the vectors λgt11 and pBTA224, using as host cells $E.coli$ strains such as JM101, JPA101 and 7118. Successful expression of the autoantigen as a fusion protein may also be achieved using the well-known PVC vectors, or using the pGEX series which give expression of glutathione S-transferase fusion proteins, again using $E.coli$ as the host cells. Alternatively, the mitochondrial autoantigen may be expressed as a non-fused polypeptide, by using appropriate vector and host cell combinations. Other vector and host cell combinations which can be used in accordance with the present invention including a number of well described yeast shuttle vectors growing in yeast cells, or eukaryotic vectors in continuous cell lines, or transgenic animals.

BRIEF DESCRIPTION OF THE DRAWINGS

The identification, cloning and expression of the 70 kd mitochondrial autoantigen of PBC in accordance with the present invention, and its use in an ELISA, will now be described in detail, with reference to the accompanying drawings in which:

FIGS. 6a–6d show the nucleotide sequence of pRMIT and deduced amino acid sequence of the 70 kd mitochondrial antigen of PBC.

FIGS. 8a and 8b show the nucleotide sequence and deduced amino acid sequence of a 2.2 kb cDNA insert that encodes the human equivalent of the sequence depicted in FIG. 6, encompassing the human equivalent of the region of nucleotides 105–1065 in FIG. 6. This human cDNA clone was obtained by probing a human placental library using pRMIT as a hybridization probe according to known techniques. The sequences are highly homologous and have comparable reactivity with auto-mitochondrial antibodies; accordingly either antigen sequence could be used as the basis of a diagnostic test to detect anti-mitochondrial antibodies or auto-reactive cells.

DETAILED DESCRIPTION OF THE INVENTION

A. MATERIALS AND METHODS

Screening cDNA library

Figure 1:
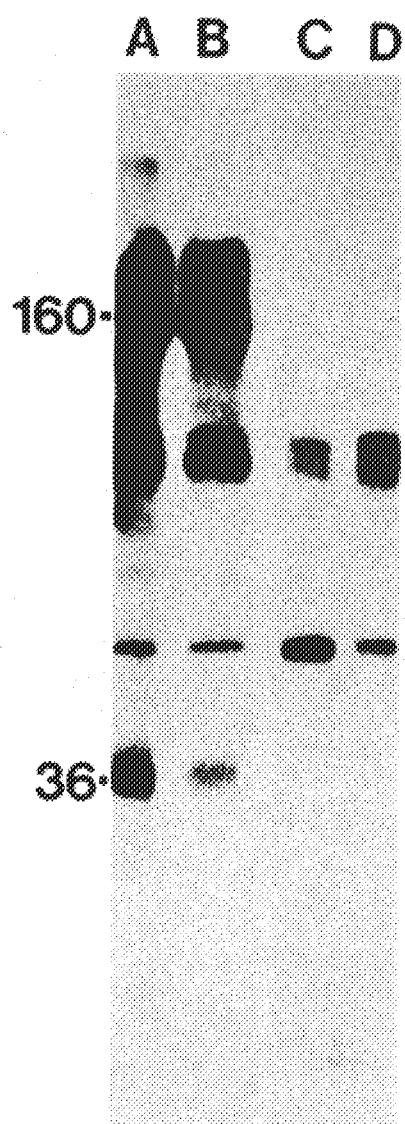
FIG. 1 shows specificity of the fused polypeptide. In lanes A and B, two different PBC sera at a dilution of 1/1000 were probed against lysates of pRMIT transformed JM101 cells. Both sera reacted with a polypeptide at 160 kd. In contrast, in lanes C and D, the same sera were nonreactive when probed against lysates of control cells containing an irrelevant insert that is also fused to β-galactosidase. The reactive bands in lanes C and D correspond to $E.coli$ proteins. Duplicate blots probed with normal sera at 1/100 and 1/1000 failed to detect the fused polypeptide and are not shown. There is some breakdown of the fusion protein with reactivity at 36 kd.

A rat liver cDNA library in λgt 11-Amp3 consisting of 15,000 recombinants, of average length of 1.4 kb, was probed by using sera from patients with PBC. The sera used for screening were from each of three patients with classical PBC who were shown to have antibodies to mitochondria by immunoblot analysis of electrophoretically separated proteins of human placental mitochondria[2]. As some patients with PBC have high-titre antibodies to E.coli, the sera were extensively preabsorbed against E.coli infected with non-recombinant phage. The sera were used for probing at a final concentration of 1:1000[11,12]. The λ-Amp3 library was incubated with E.coli, strain ST9, for 15 min at 37° C. and then was plated for 2 hr at 42° C. in LB agar. Thereafter, nitrocellulose filters that had been previously soaked in 10 ml isopropyl-thiogalactosidase (IPTC) and allowed to air dry were overlayed on each plate. The plates were then incubated overnight at 37° C. The nitrocellulose was removed after alignment and was washed for 1 hr in PBS with 5% milk powder, pH 7.4. The filters were then incubated for 45 min with previously absorbed sera of patients with PBC, washed three times for 30 min, and incubated with $^{125}$I-protein A (300,000 cpm/ml) for 45 min. Finally, the filters were washed three times, were allowed to air dry, and were placed on XRP-1 film with an intensifying screen for an overnight (12 hr) exposure. All washings and dilutions of sera and $^{125}$I-protein A were done with milk powder. Putative positive clones were picked and rescreened for plaque purification[12,13].

Subcloning

Three clones gave positive signals, a frequency of approximately one in 50,000 clones. These positive clones were plaque purified. Each of these clones yielded an identical sized insert of approximately 1.4 kd. The inserts were subcloned in the plasmid vector pBTA224, which is a high copy plasmid expression vector with a site for insertion of foreign DNA identical to that of λ-Amp3. Therefore, 50% of the subclones should also give a positive signal on an immunoassay as the insert is in the same reading frame as λ-Amp3. Clones expressing an unrelated rat liver cDNA (the F alloantigen) were used as controls. Arrays of pBTA224 colonies were prepared to identify immunoreactive clones. Colonies were incubated for 16 hr at 37° C., then were induced with 10 mM IPTG for 4 hr. The colonies were lysed and prepared for antibody probing as described[11]. Filters were probed with either a 1/1000 dilution of absorbed PBC sera or a 1/100 dilution of normal serum. One positive clone, designated pRMIT, that expressed a fused polypeptide of 160 kd was selected for further study.

Immunoblotting of mitochondrial proteins

Mitochondria from human placenta were prepared as described[2,14]. Polyacrylamide gel electrophoresis (PAGE) was performed on 1 mm-thick slab gels in 0.1% SDS, using a 3.8% stacking gel and a 10% resolving gel. Before PAGE, the purified mitochondria were suspended at a concentration of 4 mg protein/ml and were incubated for 30 min with 10,000 U of bovine pancreatic DNAse 1 at 37° C., and then were held with an equal volume of 3% aqueous octyl glucoside for 15 min at 4° C. The final preparations were diluted with Tris-HCl, pH6.8, containing 4% SDS, 20% glycerol, and 5% 2-mercaptoethanol (sample buffer) and were boiled for 5 min. Approximately 10 μg protein were loaded in each gel lane[2].

Specificity of pRMIT fused polypeptide

To demonstrate that pRMIT expressed an antigen specifically reactive with sera from patients with PBC, lysates of the expressing clone were probed with sera from healthy persons or from patients suffering from different autoimmune diseases. Briefly, a 100 ml overnight culture of JM101 cells transformed with pRMIT was diluted 1/10 in L-broth containing 10 mM IPTG. Four hours later the cultures were spun at 5000×G for 10 min and were snap frozen after addition of 20 ml of phosphate-buffered saline. PAGE was performed on 1 mm-thick slab gels with 0.1% SDS, using a 3.8% stacking gel and a 7.5% resolving gel. Samples were diluted 1/100 in the above sample buffer and were boiled for 5 min. Each lane contained approximately 5 to 10 μg of protein. The samples were probed with PBC sera diluted at 1/1000, and the reactivity was determined as above, using $^{125}$I-protein A and exposure for 18 hr. These same sera also were used to probe immunoblots of lysates of non-recombinant control clones or clones expressing a fused polypeptide coded by an irrelevant DNA insert. The sera used were from patients with PBC, systemic lupus erythematosus, rheumatoid arthritis; Sjogren's syndrome, chronic active hepatitis and from healthy normal volunteers. All control sera were studied at a dilution of 1/100.

Identification of fused polypeptide

The fused polypeptide expressed by pRMIT was characterised to determine whether it was a mitochondrial antigen recognised by PBC sera. The clone pRMIT was grown in liquid culture overnight. It was thence put into log phase and induced to give maximal expression of the fused polypeptide with 10 mM IPTG for 4 hr. Bacterial lysates were prepared as above and coupled to cyanogen bromide-Sepharose[15]. This solid support was then used as an affinity reagent to bind antibodies selectively from seven different PBC sera. First, sera from seven patients with PBC were absorbed extensively with sonicates of E.coli transformed with non-recombinant pBTA224. Thence, the sera at dilutions of 1/200, 1/2000, and 1/20,000 were passed through the lysate of pRMIT-transformed bacteria bound to a solid support. The nonabsorbed antibodies were collected, compared with unmanipulated sera at the same final dilution, and used to probe placental mitochondria, prepared as above.

Preparation of affinity-purified antibody

Affinity-purified antibody was prepared by first extensively preabsorbing five different reactive sera with sonicates of JM101, which had been transformed with non-recombinant pBTA224, and then passing this absorbed serum over a column of JM101 transformed with non-recombinant pBTA224[15]. Each serum was passed over a column of induced JM101 cells transformed with pRMIT, and the column was washed for 24 hr with 100-fold the bed volume of the column. Thence, lycine HCl was used to elute the bound antibodies[15]. The antibodies that had bound to the pRMIT absorbent were probed against fractionated placental mitochondria, a lysate of expressing pRMIT, and a lysate of a control recombinant clone. They were also reacted by immunofluorescence with either HEp-2 cells or kidney tissue sections.

Isolation of mitochondrial antigen expressed as fused polypeptide

Isolation of the fused polypeptide was performed by using gel filtration in the presence of SDS to fractionate the insoluble pellet and to obtain material suitable for immunization. A clone of pRMIT was incubated overnight at 37° C. in L-broth containing 10 $\mu$g/ml ampicillin. Eighteen hours later it was diluted for log phase growth and was induced with 10 mM IPTG for 4 hr. The E.coli preparation was then harvested at 5000×G for 10 min, and the pellets were resuspended in 40 ml of 10 mM Tris-HCl, pH8.0, containing 2 mM EDTA. Lysozyme was then added to a final concentration of 0.25 mg/ml, and the mixture was rotated for 30 min at room temperature. The solution was made up to 0.2% of Triton X-100 with continuous mixing for an additional 10 min at room temperature. An equal volume of 10 mM Tris-HCl with 2 mM EDTA, 50 mM NaCl, and 10 mM $MgCO_2$ was added with a final concentration of 2 mg/ml DNAse. This was allowed to rotate for 15 min at room temperature and then was spun at 1500×G for 5 min. The pellet was discarded and the supernatant was spun for 30 min at 10,000×G. This final pellet was then fractionated on a Sephacryl S-300 column in tandem with a Sephacryl S-400 column, after dispersion of the pellet in 0.1M phosphate buffer, pH 6.0, with 2% SDS and 10 mM dithiothreitol (DTT). The fractions were eluted at 50 ml/hr, and 6-min fractions were collected for assay by analytical SDS-PAGE and immunoblotting. SDS was finally removed on a hydroxyapatite column after dilution with 0.5M phosphate buffer, pH6.8, and 1 mM DTT. The purity of fractions was confirmed by SDS-PAGE and immunoblotting as above.

Immunization of mice

Groups of six BALB/c female mice were immunized with 10 $\mu$g of purified fused polypeptide in complete Freund's adjuvant (CFA). Three weeks later they were boosted with the same dose in CFA. Six weeks after the initial immunization, mice were bled and the sera were isolated. These sera were assayed at a dilution of 1/1000 and were probed against PAGE-separated placental mitochondria as above except that affinity-purified $^{125}$I-goat anti-mouse Ig was used. The sera were also studied at 1/100 by immunofluorescence, using sections of HEp-2 cells and kidney tissue sections as described[1,2,5].

Nucleotide and amino acid sequence

The cDNA insert of pRMIT was subcloned into M13, and the nucleotide sequence as determined[16,17]. The correct frame and orientation of the insert was determined by double-stranded sequencing of an expressing clone[17]. The sequence was determined in both orientations, and use was made of synthetic oligonucleotides to prime reactions[18].

ELISA

Briefly, the purified recombinant fused polypeptide at 2 $\mu$g/ml, diluted in carbonate buffer, was absorbed to Immulon 1 microtitre plates (Dynatech Laboratories, Alexandria, Va.) overnight at 4° C. After blocking the non-specific sites with foetal calf serum (FCS) buffer (5% FCS, 1% BSA, 0.3% gelatin in PBS), PBC sera diluted in FCS buffer, were incubated for one hour. The plates were washed three times with PBS/0.1% tween and then incubated with each of the following mouse monoclonal antibodies specific against human heavy chain isotypes: SG-11 for IgG1, GOM-1 for IgG2, SJ-33 for IgG3, SK-44 for IgG4, MB-11 for IgM and GA-1 for IgA (Miles Scientific, Naperville, Ill.). The binding of mouse MoAbs were detected with peroxidase conjugated goat anti-mouse IgG (Tago, Bulingame, Calif.) for all except SJ-33 which was detected with peroxidase conjugated goat anti-mouse IgM (Tago, Burlingame, Calif.). ABTS was used as the colour substrate for the peroxidase. For detection of all isotypes of AMA, HRP-G Hulg was used in the place of isotype specific monoclonals.

Human myeloma proteins were used to obtain the optimal dilutions of the isotype specific MoAbs. Predetermined dilutions of myeloma proteins were coated onto microtitre plates and ELISA performed as before with serial dilutions of isotype specific MoAbs followed by the peroxidase conjugated reagents. The dilutions of isotype specific MoAbs which gave similar O.D. units at approximately equal serum isotype concentrations were used in the ELISA.

To obtain the optimal serum dilutions for screening, previously screened (by immunofluorescence) AMA-positive PBC, progressive sclerosing cholangitis and normal sera were titrated by the ELISA. It was found that a serum dilution of 1:1000 yielded the highest signal to noise ratio, and this dilution was used to obtain all results. The cut-off point for negatives were determined as 2 standard deviation above the mean O.D. of normal sera.

B. RESULTS

Arrays of pRMIT in BTA224

Subclones of pRMIT in JM101 were very immunoreactive when probed with sera from patients with PBC, whereas control clones were nonreactive. In contrast, sera from normal volunteers reacted with neither pRMIT in JM101 nor control clones. Positive colonies from arrays were used in all subsequent studies.

Specificity of pRMIT fused polypeptide

Sera at dilutions of 1/1000 from 25 of 25 patients with PBC reacted with a 160 kd fused polypeptide made in pRMIT (Table I and FIG. 1). This band also reacted with a rabbit antiserum to β-galactosidase (data not shown). A number of bands corresponding to components of lower m.w. also were recognised, including one at approximately 36 kd, which was apparently a breakdown product of the 160 kd molecule. These lower m.w. materials were only associated with pRMIT and were immunoreactive with PBC sera. The titre of reactivity for these 25 sera ranged from 1:1000 to 1:1,000,000. With the use of the same 25 sera, the fused polypeptide was not detected in lysates of bacteria produced by non-recombinant pBTA224 or bacteria transformed with an irrelevant insert and induced to express an abundant fused polypeptide. None of the sera from patients with systemic lupus erythematosus, rheumatoid arthritis, or chronic active hepatitis reacted with the fused protein at dilutions of 1/100, even with autoradiographic exposures of up to 4 days.

TABLE 1

Reactivity of human sera with the pRMIT fused polypeptide.

| Group[a] | No. positive[b]/Total |
|---|---|
| PBC | 25/25 |
| Normal persons | 0/25 |
| Systemic lupus erythematosus | 0/21 |
| Rheumatoid arthritis | 0/18 |
| Chronic active hepatitis | 0/32 |

[a]PBC sera were studied at 1/1000 sera dilution; other groups were studied at 1/100 sera dilution.
[b]A positive blot was one in which reactivity to a band of 160kd was readily visible after an autoradiographic exposure level of 12 hr. See FIG. 1.

Identification of fused polypeptide

Figure 2:
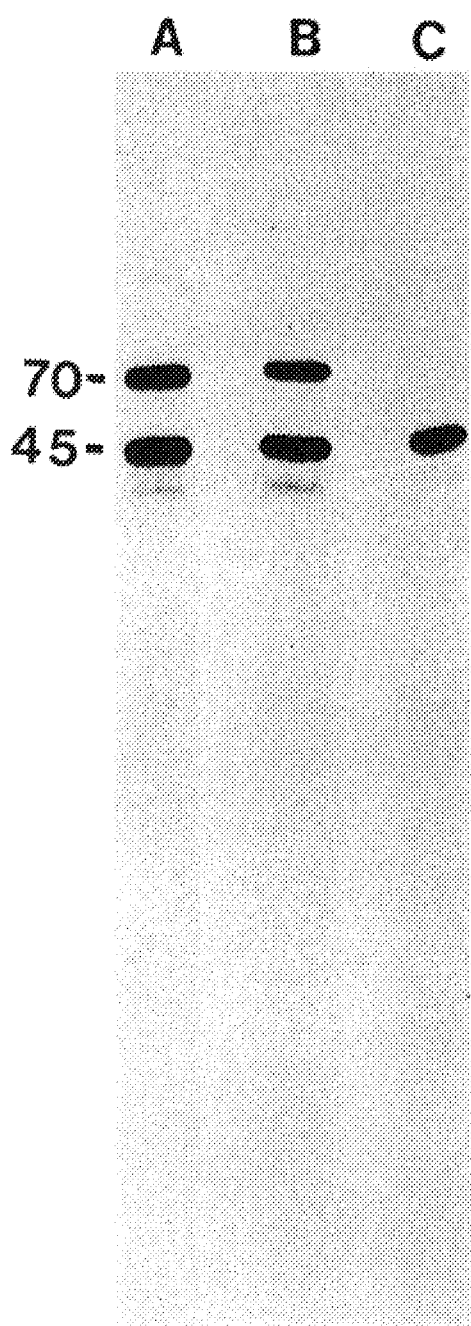
FIG. 2 shows identification of the pRMIT fused polypeptide. The reactivity of absorbed and unabsorbed PBC serum against human placental mitochondrial proteins after PAGE was determined. In lane A, the probe was an unabsorbed PBC serum at a final dilution of 1/2000. In lane B, the probe was the same serum at a final dilution of 1/2000 after extensive absorption for 72 hr against cells transformed with non-recombinant pBTA224 and passage over a solid support to which had been bound a lysate of cells transformed with non-recombinant pBTA224. In lane C, the probe was the same serum at a final dilution of 1/2000 after absorption for 72 hr against cells transformed with non-recombinant pBTA224 and passage over a solid support to which had been bound a lysate of cells transformed with expressing pRMIT. The serum was also studied at 1/200 and 1/20,000 (Table II).

After absorption with the lysate of pRMIT, sera from all seven patients with PBC were shown to be depleted of antibodies reactive with the 70 kd antigen (Table II). In contrast, such absorption did not change the reactivity to the 45 kd or 39 kd antigen. No such depletion was seen when PBC sera were absorbed against a lysate of a control clone bound to a solid support. The finding that the reaction of PBC sera with the pRMIT fused polypeptide appeared to remove detectable anti-70 kd reactivity indicates that the cDNA encodes all determinants recognised by the autoantibodies to the 70 kd antigen (Table II; FIG. 2).

Affinity-purified antibodies

Figure 3:
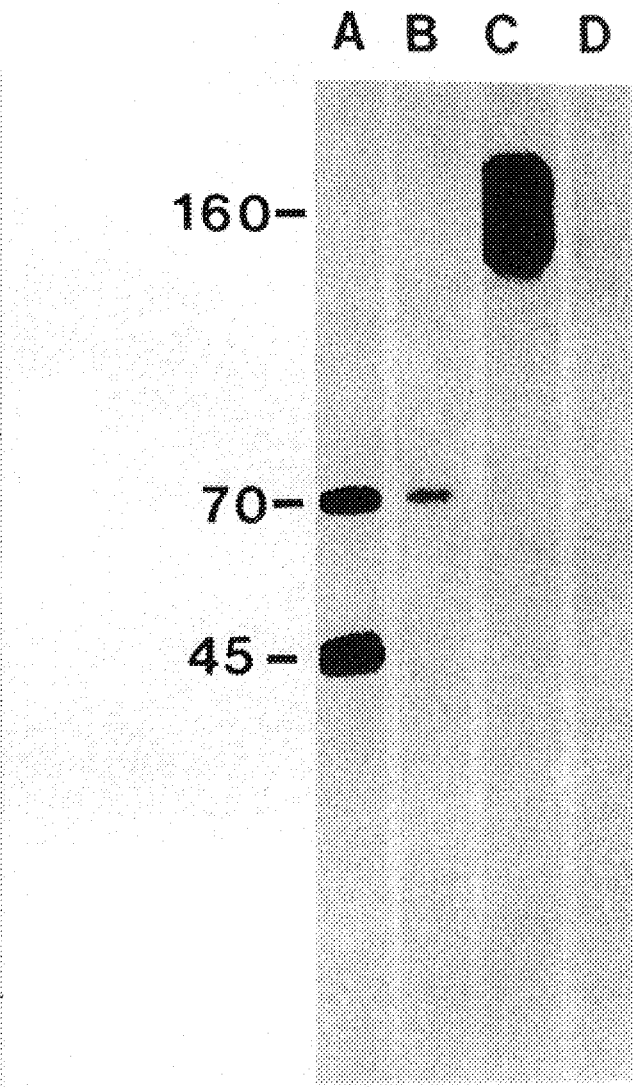
FIG. 3 shows specificity of affinity-purified antibody. In lane A, an unabsorbed PBC serum at 1,2000 was probed against placental mitochondria, reacting with both the 70 and the 45 kd protein. In lane B, the column eluate was probed against the same mitochondrial preparation. Note the reactivity was only to the 70 kd protein, and the reduction in signal correspond to the expected recovery for such elution. Even on a very long autoradiographic exposure time of 1 wk, there remained activity only to the 70 kd protein (data not shown). In lane C, the eluate was probed against a sonicate of induced JM101 transformed with pRMIT. The intensity of the 160 kd fused polypeptide was due to the large quantity of fused polypeptide expressed. In lane D, the eluate was probed against a sonicate of induced JM101 transformed with an irrelevant plasmid that encodes an abundant fused polypeptide.

The eluted antibodies of five different PBC sera reacted with the 70 kd polypeptide of fractionated placental mitochondria and with the 160 kd fused polypeptide in pRMIT (FIG. 3), further indicating that pRMIT encodes the 70 kd antigen. The eluted antibodies did not react with a lysate of bacterial proteins from a clone expressing a control liver cDNA. The eluted antibodies also gave a characteristic pattern of anti-mitochondrial staining by immunofluorescence with either HEp-2 cells or kidney tissue sections.

Immune response of mice

Figure 4:
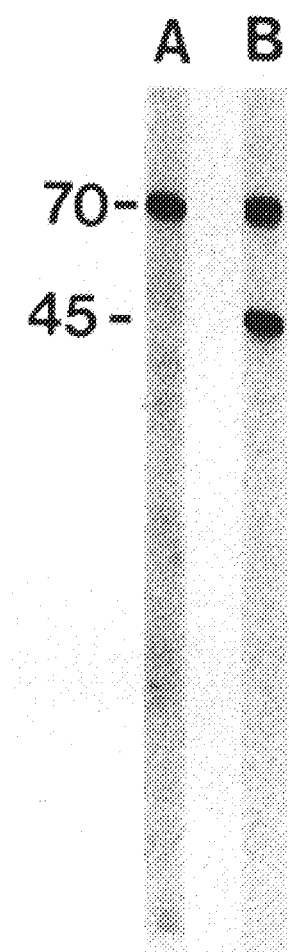
FIG. 4 shows immune response of BALB/c mice immunized with pRMIT induced fused polypeptide. Placental mitochondria were separated by PAGE on a 7.5% gel and blotted onto nitrocellulose, and the fractionated proteins were probed with sera at a dilution of 1/1000 (lane A) or with serum from a patient with PBS at 1/1000: immunized mice produced antibody against the 70 kd but not the 45 kd protein.
Figure 5:
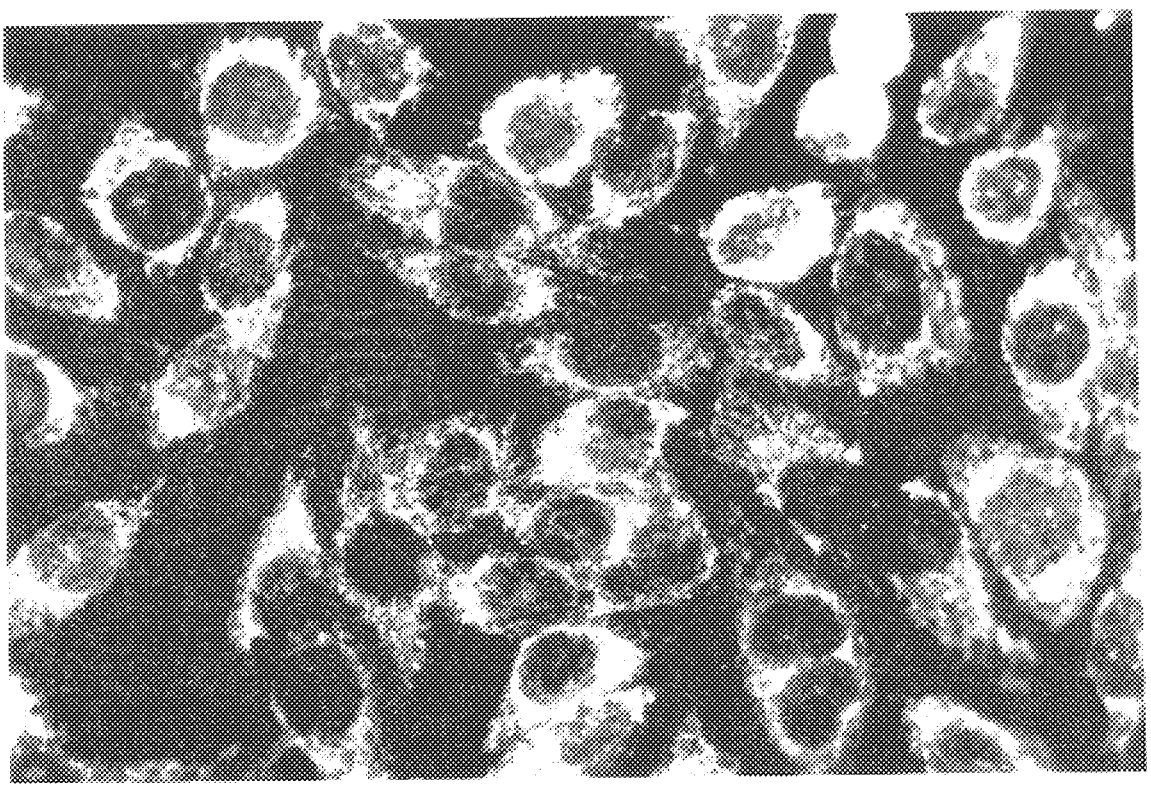
FIG. 5 shows immunofluorescence of HEp-2 cells. BALB/c mice were immunized with the purified fused polypeptide and sera incubated with HEp-2 cells. Note the typical mitochondrial pattern of reactivity.

BALB/c mice, after injection of the pRMIT fused polypeptide, gave an antibody response to the 70 kd placental mitochondrial protein. Control nonimmunized mouse sera was nonreactive (FIG. 4). In addition, these sera produced a typical pattern of anti-mitochondrial immunofluorescence on both HEp-2 cells and kidney tissue sections (FIG. 5).

Nucleotide and amino acid sequence

The insert is 1370 base pairs long and consists entirely of coding region (FIG. 6). The 456 amino acids would code for a polypeptide of approximately 48 kd, consistent with the observed size of the fused polypeptide produced by the clone; it is thus not a full-length sequence of the antigen. The sequence contains 11% proline, and the proline is frequently found preceded by short stretches of hydrophobic amino acids such as alanine and valine, e.g., from nucleotides 54 to 102. Comparison of the sequence of the 70 kd mitochondrial autoantigen with known protein and DNA sequences did not reveal any closely homologous sequences. The sequence is not present in mitochondrial DNA (data not shown), and the 70 kd protein is therefore coded for by nuclear genes.

Figure 7:
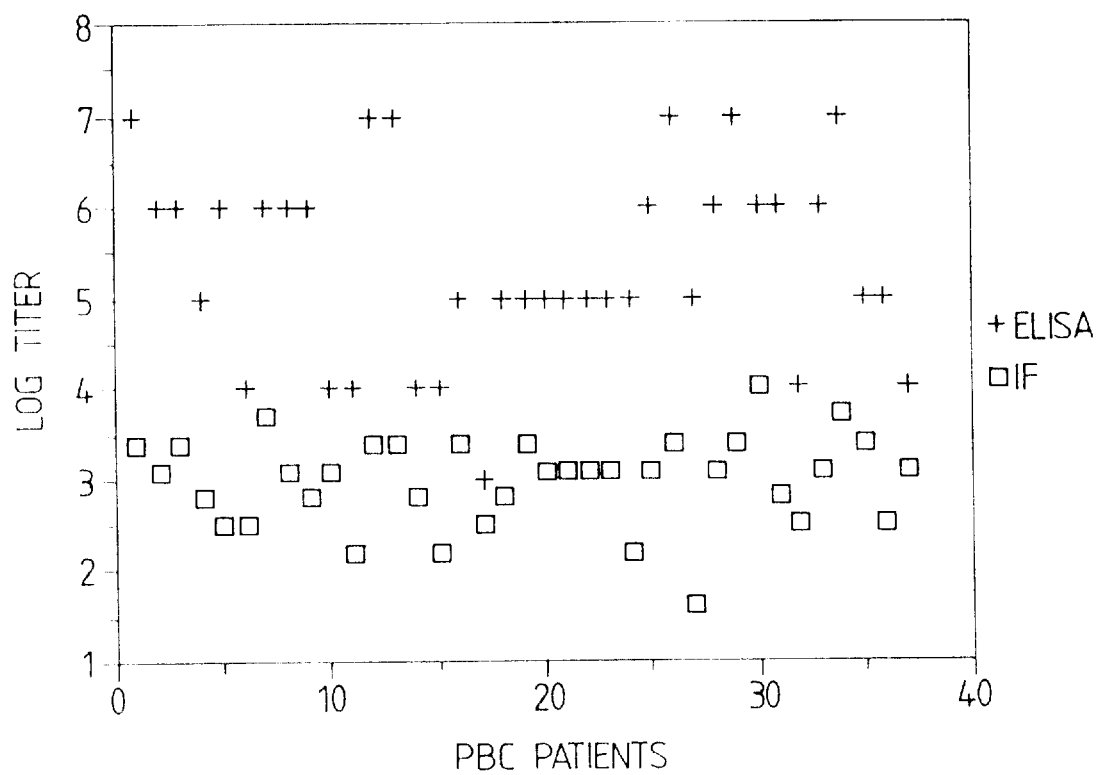
FIG. 7 shows comparison of sensitivity between the ELISA (+) and immunofluorescence (□) in detection of AMA in PBC. PBC sera were tested at every 10 fold dilution stating from 1:1000 in the ELISA whereas in the immunofluorescence against Hep-2 cells every 2 fold dilution starting from 1:10 was used. The positives on ELISA were defined as 2 S.D. O.D. units above the mean for normal sera.

The sensitivity of ELISA was compared with immunofluorescence for 37 patients with PBC (FIG. 7). ELISA was found to be approximately 250 fold more sensitive; the average titre detected by ELISA was $10^{5.4}$ whereas by immunofluorescence it was only $10^3$.

TABLE II

Absorption of PBC sera with the pRMIT fused polypeptide

| Pa-tient | Preabsorption Titre[a] | | | Postabsorption Titre[a] | | |
|---|---|---|---|---|---|---|
| | 70kd | 45kd | 39kd | 70kd | 45kd | 39kd |
| 1 | 1:2,000 | 1:2,000 | 0 | 0 | 1:2,000 | 0 |
| 2 | >1:20,000 | 1:20,000 | 0 | 1:200 | 1:2,000 | 0 |
| 3 | >1:20,000 | >1:20,000 | 1:2,000 | 1:200 | >1:20,000 | 1:2,000 |
| 4 | 1:2,000 | 1:200 | 0 | 0 | 1:200 | 0 |
| 5 | >1:20,000 | >1:20,000 | 1:2,000 | 1:200 | >1:20,000 | 1:2,000 |
| 6 | 1:2,000 | 0 | 0 | 0 | 0 | 0 |
| 7 | >1:20,000 | 1:2,000 | 0 | 0 | 1:2,000 | 0 |

[a]Reactivity on immunoblots using placental mitochondria as described; absorption with control lysates does not influence the titre.

REFERENCES

1. Berg, P. A., Klein, R. and Lindenborn-Fotinos, J. J. Hepatology 2:123–131, 1986.
2. Frazer, I. H., Mackay, I. R., Jordan, Wittingham, S. and Marzuki, S. J. Immunol 135:1739–1745, 1985.
3. Kenna, J. G., Neuberger, J., Davies, E., Eddleston, A. L. W. F., and Williams, R. J. Immunol. Methods 73:401–413, 1984.
4. Kaplan, M. M., Gandolfo, J. V., Quaroni, E. G. Hepatology 4:727–730, 1984.
5. Walker, J. G., Doniach, D., Roitt, I. and Sherlock, S. Lancet 1:827–831, 1965.
6. Lindenborn, Fotinos, J., Baum, H. and Berg, P. A. Hepatology 5:763–769, 1985.
7. Mendel-Hartvig, I., Nelson, B. D., Loof, L., and Totterman, T. J. Clin. Exp. Immunol. 62:371–379, 1985.
8. Baum, H. and Palmer, C. Mol.Aspects Med. 8:201, 1985.
9. Miyachi, K., Watanabe, S., Yamashiki, Hiwatashi, T. and Ichida, F. Am.J.Gastro. 79:704–709, 1984.
10. Uzoegwu, P. N., Baum, H. and Williamson, J. Cell Biol. Intl. Reports 8:987–992, 1984.
11. Kemp, D. J., Coppel, R. L., Cowman, A. F., Saint, R. B., Brown, G. V. and Anders, R. F. Proc.Natl.Acad.Sci.USA 80:3787–3791, 1983.
12. Young, A. A. and Davis, R. W. Science 222:778, 1983.
13. Stahl, H. D., Coppel, R. L., Brown, G. V., Saint, R., Lingelbach, K., Cowman, A. F., Anders, R. F. and Kemp, D. J. Proc.Natl.Acad.Sci. USA 81:2456, 1984.
14. Hare, J. F., Ching, E. and Attardi, G. Biochemistry 19:2023–2027, 1980.

15. Crewther, P. E., et. al. *J.Immunol.Meth.* 86:257–264, 1986.
16. Messing, J. and Vieira, J. *Gene* 19:269–276, 1982.
17. Sanger, F. *Science* 214:1205, 1981.
18. Vieira, J. and Messing, J. *Gene* 19:259, 1982.
19. Smith, N. D. and Boyer, J. L. *Hepatology* 6:739, 1986.
20. Hurt, E. C. and vanLoon, A. P. G. M. *Trends Biochem..Sci.* 2:204, 1986.
21. Anderson, S., Bankier, A. T., Barrell, B. G., deBruiin, M. H. L, Coulson, A. R., Drouin, J., Eperon, I. C., Nierlich, D. P., Roe, B. A., Sanger, F., Schreier, P. H., Smith, A. J. H., Staden, R. and Young, I. G. *Nature* 290:457, 1981.
22. Andereson, S., deBruiin, M. H., Coulson, A. A., Eperon, I. C., Sanger, F. and Young, I. G. *J.Mol.Biol.* 156:683, 1982.
23. Berg, P. A. and Baum, H. *Sem.Immunopath.* 3:355–373, 1980.
24. Klein, R., Lindenborn, J. and Berg, P. A. *J.Immunol..Methods* 64:227–238, 1983.
25. Miyachi, K., Gupta, R. C., Dickson, E. R. and Tan, E. M. *Clin.Exp.Immunol.* 39:599–606, 1980.
26. Munoz, L. E., Thomas, H. C., Scheurer, P. J., Doniach, D. and Sherlock, S. *Gut.* 136–140, 1981.
27. Taal, B. G., Schalm, S. W., Ten Kate, F. W. J., Hermans, J., Geertzen, R. G. and Feltkamp, B. E. W. *Hepato-Gastro.* 30:178–182, 1984.
28. Eriksson, S. and Lindgren, S. *Scand.J.Gastro.* 19:971–976, 1984.
29. Berg, P. A., Wiedmann, K. H., Sayers, T., Kloppel, G. and Lindner, H. *Lancet* 1:1329, 1980.
30. Weber, P., Brenner, J., Stechemesser, E., Klein, R., Weckenmann, U., kloppel, G., Kirchhof, M., Fintelmann, V. and Berg, P. A. *Hepatology* 6:553, 1986.
31. Modena, V., Marengo, C., Amoroso, A., Rosina, F., Costantini, P., Bellando, P., Coppo, R. and Rizzetto, M. *Clin.Exp.Rheumatol.* 4:129, 1986.
32. Udeenfelt, F. and Danielsson, A. *Ann.Clin.Res.* 1:148, 1986.
33. Schultheiss, H.-P., Berg, P. A. and Klingenberg, M. *Clin.Exp.Immunol.* 58:596, 1984.
34. James, S. P., Hoofnagle, J. H., Strober, W. and Jones, E. A. *Ann.Int.Med.* 99:500, 1983.
35. Namihisa, T., Kuroda, H. and Imanari, H. *Jpn.Soc.Gastroenterol.* 18:445, 1983.
36. Van den Oord, J. J., Fevery, J., De Groote, J. and Desmet, V. J. *Liver* 4:264, 1984.
37. Shimizu, M., Yuh, K., Aoyama, S., Ichihara, I., Watanabe, H., Shilo, H. and Okumura, M. *Liver* 6:1, 1986.
38. Avigan, M. I., Adamson, G., Hoofnagle, J. H. and Jones, E. A. *Hepatology* 6:999, 1986.
39. Fennell, R. H. *Pathol.Annu.* 16(Pt.2):289, 1981.
40. Neuberger, J., Portmann, B., Macdougall, B. R. D., Calne, R. Y. and Williams, R. *N.Engl.J.Med.* 306:1, 1982.
41. Handley, H. H., Glassy, M. C., Cleveland, P. H. and Roystan, I. *J.Immunol.Meth.* 54:291–298, 1982.
42. MacDonald, R. A., Hosking, C. S. and Jones, C. L. *J.Immunol.Meth.* In press, 1987.

We claim:

1. An isolated polypeptide consisting of the amino acid sequence of FIGS. 6(*a*)–6(*d*) or an antigenic fragment of said sequence.

2. An isolated polypeptide consisting of the amino acid sequence encoded by nucleotides 76–679 as shown in FIGS. 6(*a*)–6(*d*).

3. An isolated polypeptide consisting of the amino acid sequence AEIETDKATIGFEVQEEGYL.

4. An isolated antigenic fragment of a 70 kD mitochondrial autoantigen of primary biliary cirrhosis comprising the amino acid sequence of FIGS. 6(*a*)–6(*d*).

5. An isolated polypeptide consisting of the amino acid sequence of FIGS. 8(*a*)–8(*b*) or an antigenically active fragment of said sequence.

6. An isolated antigenic fragment of a 70 kD mitochondrial autoantigen of primary biliary cirrhosis comprising the amino acid sequence of FIGS. 8(*a*)–8 (*b*).

7. An isolated antigenic fragment of a 70 kD mitochondrial autoantigen of primary biliary cirrhosis comprising the amino acid sequence encoded by nucleotides 76–679 of FIGS. 6(*a*)–6(*d*).

8. An isolated antigenic fragment of a 70 kD mitochondrial autoantigen of primary biliary cirrhosis comprising the amino acid sequence AEIETDKATIGFEVQEEGYL.

9. An ex vivo method of treating a patient suffering from primary biliary cirrhosis (PBC) which comprises:
   (a) immobilizing a polypeptide of any one of claims 1–3 on a solid support;
   (b) extracorporeally contacting plasma from said patient with said immobilized polypeptide in a manner and for a time sufficient to permit adsorption of PBC-associated autoantibodies from said plasma; and
   (c) returning the adsorbed plasma to said patient.

* * * * *